United States Patent [19]

Ams et al.

[11] Patent Number: 4,841,363
[45] Date of Patent: Jun. 20, 1989

[54] ENDOSCOPIC VIDEO SYSTEM

[75] Inventors: Felix Ams, Kämpfelbach; Roland Schäfer, Bretten-Diedelsheim, both of Fed. Rep. of Germany

[73] Assignee: Richard Wolf GmbH, Fed. Rep. of Germany

[21] Appl. No.: 219,441

[22] Filed: Jul. 14, 1988

[30] Foreign Application Priority Data

Jul. 14, 1987 [DE] Fed. Rep. of Germany ....... 3723228

[51] Int. Cl.$^4$ ............................................... A61B 1/04
[52] U.S. Cl. ........................................ 358/98; 128/6; 358/148; 358/183
[58] Field of Search ................. 358/98, 183, 148, 149, 358/153; 128/6

[56] References Cited

U.S. PATENT DOCUMENTS

| 4,654,701 | 3/1987 | Yabe | 358/98 |
| 4,727,417 | 2/1988 | Kanno | 358/98 |
| 4,768,089 | 8/1988 | Kato | 358/98 |

Primary Examiner—Howard W. Britton

[57] ABSTRACT

An endoscopic television system includes: a character generator which is controlled by a keyboard to store characters selected by actuation of the keyboard in a character store; an image control trigger by synchronization pulses derived from an endoscopic image video signal to read out the stored characters in the character store and to generate a character video signal; a mixer for mixing the endoscopic image video signal and the character video signal to generate a composite signal that is supplied to a television monitor. The characters are displayed on the television monitor in the portion of the screen not occupied by the endoscopic image.

18 Claims, 2 Drawing Sheets

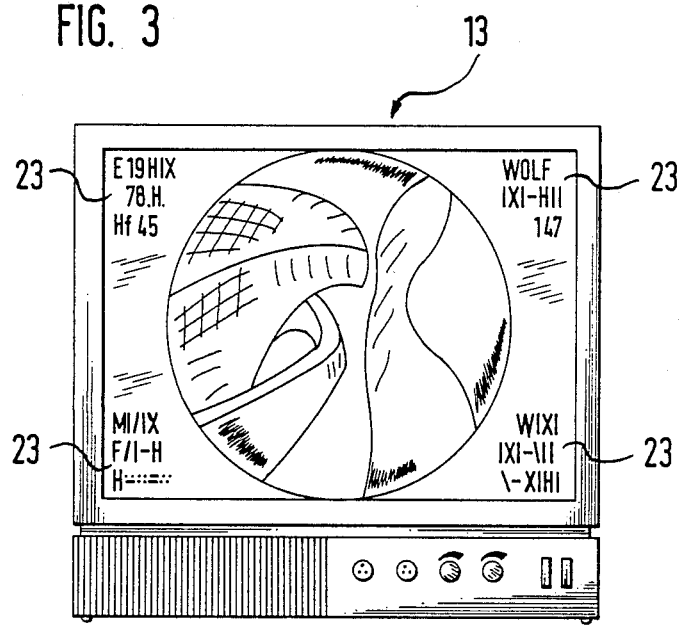

ENDOSCOPIC VIDEO SYSTEM

BACKGROUND OF THE INVENTION

The present invention relates generally to endoscopic television systems in which an endoscopic image is: picked up by an endoscope by way of an optical system or a semiconductor image convertor integrated in the endoscope; supplied as a video signal to a television monitor; and then displayed on a portion of the television monitor screen in the form of a circular endoscopic image, other portions of the screen being left free of images. The invention relates specifically to an endoscopic television system, as described, including means and methods for correlating the endoscopic image with documentary information concerning patient data and operating characteristics of related apparatus in which the documentary information is mixed in with the video signal and supplied to the television monitor so that the information is displayed in the image-free edge zones of the screen of the television monitor alongside of the endoscopic image.

Endoscopic television systems are disclosed in U.S. Pat. No. 4,439,030 and German Patent DE-PS No. 34 36 057 in which video signals representative of endoscopic images are generated by television cameras or semiconductor image convertor devices such as a charge coupled device (CCD) incorporated within endoscopes. The phrase "endoscopic image" refers throughout this specification to any image, a signal representative of which, is generated by a suitably adapted endoscope. The video signals are transmitted to suitable display apparatus such as television monitors on which the endoscopic images are then displayed. In all of these endoscopic television systems, an endoscopic image is displayed on a portion of a rectangular monitor screen substantially in the form of a circular image, the remaining portion or portions of the screen being image free and defining what is referred to herein as image-free edge zones surrounding the endoscope image.

During an endoscopic inspection, certain patient-specific data or information, such as the patient's name and age, as well as the time of the inspection, and the like, have to be recorded, so as to be correlated with the specific endoscopic image displayed. Also, certain apparatus-specific characteristics data, as well as certain operating characteristics data of external patient treatment apparatus, if, for example, an operative or therapeutic intervention accompanies the endoscopic inspection, have to be associated with the displayed image, for the same reason.

In the past, the above-mentioned data or information, i.e., the information necessary for the documentation of the endoscopic inspection, either have been recorded on a separate recording medium and then correlated with an image after the inspection, or have been incorporated in the displayed image in the form of a separate partial image, for example, in the form of a rectangular fade-in into the displayed image.

Both of these methods are disadvantageous. On the one hand, upon recording documentation data separately from the endoscopic image, a specific correlation to the video image has subsequently to be carried out. This is very time consuming and requires considerable apparatus and manual work expenditure. On the other hand, the fading in of a partial television image onto the endoscopic image requires the use of a separate trick mixing desk and a separate input or convertor device to convert the documentation information into video signals and to fade-in the same by way of the trick mixing desk in the form of a partial image overlapping the overall image.

SUMMARY OF THE INVENTION

The present invention provides an endoscopic television system with which the image-free edge zone regions surrounding an endoscopic image on a substantially rectangular screen of a television monitor can be filled with documentation information which arises in connection with an endoscopic inspection and any accompanying surgical or therapeutic treatment. Simple devices are used so that additional separate devices for documentating the inspection or procedure are not necessary.

To this end, the invention provides an endoscopic television system, in which an endoscopic image of a representative object is picked up by a television camera with an optical system or a semiconductor image convertor integrated in the endoscope, and is supplied as an endoscopic image video signal to a television monitor where it is displayed as a circular image, leaving image-free edge zones on the screen of the monitor about the circular image. The system includes a character generator that is controllable with a keyboard, and that stores character signals, selected by actuation of the keyboard, in a character store or memory; an image control that is operatively triggered by synchronization pulses derived from the endoscopic image video signal in order to read out the stored character signals from the character store and to supply the same to an input of a mixer as a character video signal, to another input of which is supplied the image video signal; and an output of the mixer which carries a composite endoscopic image/character video signal that is connected to the monitor, the character generator being so programmed that the character signals are reproduced in at least one of the above-mentioned image-free edge zones on the monitor screen.

In an embodiment of the present invention, the image control is controlled by a microprocessor that converts the keying code of the signals arriving from the keyboard into the character signals and places same into a character store as a function of a program residing in a program store or memory so that the character signals, which are to be read out, are reproduced in at least one of the image-free edge zones. Basically, the image control can be controlled by any desired fixedly-programmed or computer-assisted control, for example, an external computer which collaborates with the image control. However, it has been shown that, by providing a microprocessor in the television system, adaptability to instantaneous inspection of measured characteristics of accompanying surgical or therapeutic measures is increased, since, on the one hand, the program can be rapidly adapted to accommodate the appropriate data and, on the other hand, the control by an external computer sometimes impedes flexible use of the television system.

In another embodiment of the television system, measurements and/or operating characteristics, that are generated externally to the system are written into the character store and read out therefrom for display on the monitor. To do this, the television system has one or more separate inputs, so that, for example, certain operating characteristics of apparatus supplied during the endoscopic inspection or other operation or therapy can be faded-in. In addition to this, the measurements and/or operating characteristic data that are faded-in can also stem from the television system itself, so that medical personnel can be constantly informed, during the inspection, regarding the orderly operation or functional state of the television system.

Preferably, the measurement and/or operating characteristic data input can be generated by auxiliary devices that are necessary for a predetermined endoscopic or surgical intervention, for example, anesthesia, analgesia, or surgical devices, in order to have a constant and exact documentation of the inspection, so that persons carrying out such investigations and interventions can view and determine all of the essential measurements or characteristics at a glance.

In yet another embodiment, an audible signal is generated by the television system if predetermined limits of the measurements and/or operating characteristics are exceeded, so that, for example, during inspections that require the complete attention of the operator, an out-of-range measurement or operating characteristic does not go unnoticed.

This same result is preferably achieved in that an out-of-range measurement or operating characteristic is emphasized optically on the monitor display, for example, by an alternating light/dark keying of the displayed data or a cyclical brighter keying of the displayed data.

Further, the present invention provides in yet another, that the conjunctive image of the endoscopic and character images is stored on a signal storage device. Therefore, continuously or at specific intervals of time, an exact reproduction of the entire monitor image is possible. This results in an unequivocal correlation between an endoscopic image and the documentary information.

The advantages of a television system, in accordance with the present invention, are that separate devices such as a trick mixing desk and additional signal/image convertors are not necessary and that two or more image regions, separate from one another, are available in the image-free zones surrounding the endoscopic image region on the monitor display. Additionally, as a result of different program controls, the types of parameters to be input and displayed on the image-free edge zones can be varied, since changes need be made only in the computer software or program. Thus, all of the documentation information representable on the monitor in the image-free zones is at any instant correctly correlated with the endoscopic image.

BRIEF DESCRIPTION OF THE DRAWINGS

In the drawings:

FIG. 3 is a front view of a monitor screen of the television system of FIG. 1 on which an endoscopic image is shown in the center of the screen and on which character images are shown in the image-free edge zones surrounding the endoscopic image.

DESCRIPTION OF THE PRESENTLY PREFERRED EMBODIMENT

In accordance with the invention, an endoscopic television system is provided in which character information representing documentary information relating to patient data and/or operating characteristics of associated apparatus is displayed on a monitor in image-free edge zones surrounding a circular endoscopic video image.

Figure 1:
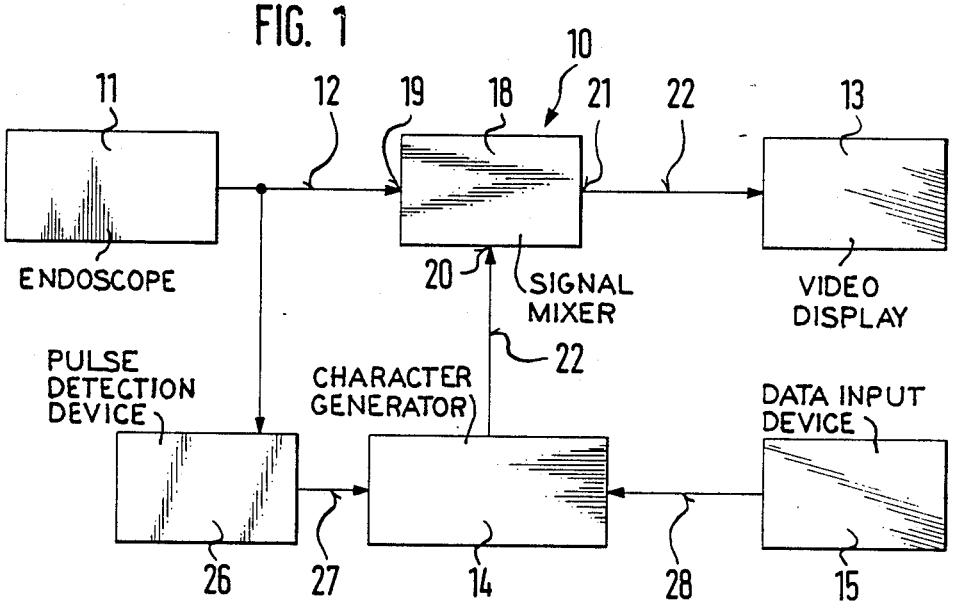
FIG. 1 is a block diagram of an endoscope television system, constructed in accordance with the invention.

As illustrated in FIG. 1, an endoscopic television system 10 fashioned in accordance with the invention includes an endoscope adapted to generate an endoscopic image video signal representative of an endoscopic image by means of an image generator 11, which can be either a conventionally constructed video signal pick-up system such as a television camera having an optical system or a semiconductor image convertor such as a charge coupled device (CCD). The system 10 further includes a monitor or video display 13 to which the endoscopic image video signal 12 is transmitted. A signal mixer 18 is connected between the monitor 13 and the image generator 11 so that the endoscopic image video signal 12 supplied by the image generator 11 is transmitted to one input 19 of the mixer 18, while an output 21 of the mixer 18 supplies an image video signal 220 to the monitor 13. The image video signal 220 includes endoscopic image information and character information supplied by a character signal 22 which is coupled to an input 20 of the mixer 18.

The endoscopic image video signal 12 supplied by the television camera 11 includes television synchronization pulses therein. Therefore, the signal 12 is coupled to a synchronization pulse separation or detection device 26, the output of which in turn supplies synchronization pulses signal 27 to a character generator 14. As described more fully below, the character generator 14 utilizes the synchronization pulses to provide read out of character information stored by the character generator 14 that is in synchronization with the endoscopic image video signal.

A data input device 15 is coupled to the character generator 14 so that a keying signal 28 corresponding to character keying codes is supplied to the character generator whenever character information is to be displayed on the television monitor or video display 13. The output of the character generator 14 supplies the character signal 22 which is transmitted to the second input 20 of the mixer 18. The data input device 15 can be any suitably adapted device such as a data output circuit of a measuring apparatus or other data generating device.

In the preferred embodiment, the data input device 15 is a keyboard capable of generating keyboard character keying codes. Further, the data input device 15, especially in the form of a keyboard, can be used to control the operation of the character generator 14 so that certain command sequences of keying codes will cause a change in the operation or running of the character generator 14 or of the displayed composite image. As can be appreciated, any keyboard that generates keying codes for any type of keyboard characters can be utilized.

The endoscopic image video signal 12 and the character signal 22 are mixed by the signal mixer 18 to generate the image video signal 220. The image signal 220 thus supplies an image for the entire screen of the video display or monitor 13, the image including both an endoscopic image and character information.

In operation, a sequence of endoscopic image video signals 12 is supplied from the image generator 11 to the mixer 18 and to the synchronization pulse separation device 26. The synchronization pulses in the signal 9 are detected by the synchronization pulse separation or detection device 26 which, in turn, supplies the synchronization pulse signal 27 to the character generator 14. The synchronization pulses in the signal 27 are used for synchronized reading of characters from a character store 16, if present, in the character generator 14.

Figure 2:
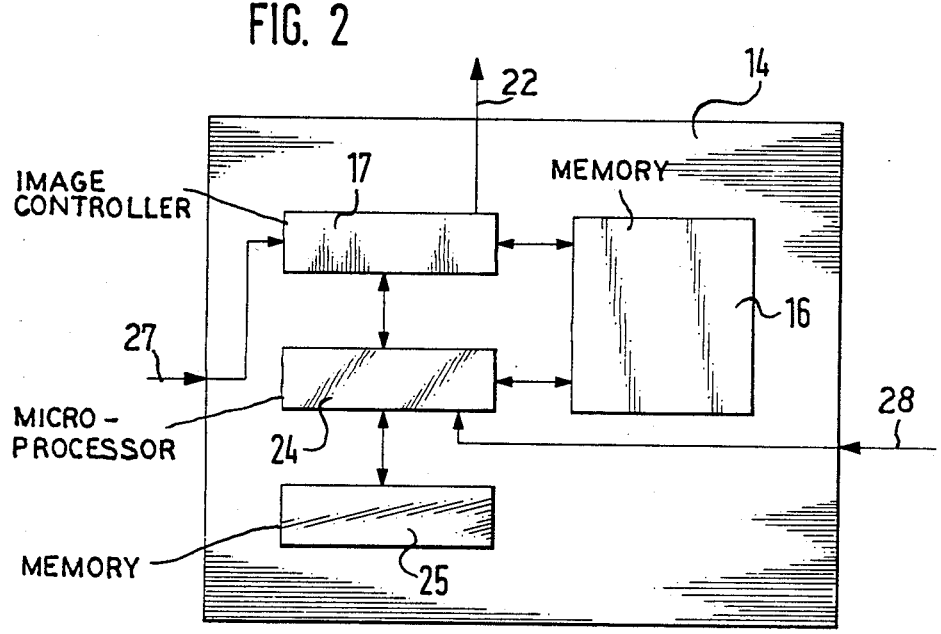
FIG. 2 is a block diagram of a character generator used in the television system of FIG. 1.

In accordance with the generation of data by the data input device 15, such as the depression of keys of a keyboard, keying signals 28 are transmitted to the character generator 14. As illustrated in FIG. 2, in the presently preferred embodiment, the signals 28 are specifically directed to a microprocessor 24 associated with the character generator 14. The microprocessor 24 is controlled by a software program stored in a suitable memory or program store such as a programmable read only memory device (PROM) 25 and to generate signals representative of the keyboard characters that are stored in a character store or memory 16. PROM 25 can easily be replaced to thus allow the implementation of different programs depending on the type of representation of characters to be made visible on the television monitor or video display 13.

As further illustrated in FIG. 2, the microprocessor 24 communicates with an image controller 17, that receives the synchronization pulses signal 27 from the synchronization pulse separation or detection device 26. The microprocessor 24 and the image controller 17 both communication with the character store or memory 16 so that the image controller reads out the characters stored in the character store or memory 16 and then generates a character video signal 22 that is displayable on a television or video monitor. The character video signal 22 is applied as the output 22 of the image controller 17 to the second input 20 of the mixer 18.

The keying signals 28 coming from the data input device 15 are positioned on the screen of the video display or monitor 13 by the microprocessor 24 in accordance with a protocol established by the program stored in the PROM 25. Specific storage locations within the character store or memory 16 correlate to specific locations on the screen of the television monitor or video display 13. Thus, by altering the protocol of the stored microprocessor program, by inputting command sequences through the data input device 5 as described above, the character signals can be placed in various storage locations within the character store 16 and this can be displayed at different locations on the screen of the television monitor or video display 13.

The character information incorporated into the character video signal 22 is read out from the character store or memory 16 by the image controller 17 and converted into the television compatible character video signal 22 and is passed to the mixer 18 in synchronization with the endoscopic image video signal 12 in accordance with the synchronization pulses signal 27. Thus, the mixer 18 mixes the endoscopic image video signal 12 with the character video signal 22 to generate the signal 220 so that both signals are displayed on the television monitor or video display 13 simultaneously in an image.

The character generator 14, in accordance with the program stored in the PROM 25, prevents the region of the substantially circular reproduction of the endoscopic image from being written over by the characters that have been input from the data input device 15. This means, that the characters generated by the data input device 15 can only be reproduced in the image-free edge zones 23 of the screen of the video display or monitor 13, as illustrated in FIG. 3.

Although not shown separately here, the character generator 14 can be provided with additional inputs into which measurements and/or operating data characteristics of other data generating devices can be directed. The data input device 15 is intended to be merely representative of the type of device used to input character data into the character generator 14. The measurements and/or operating characteristics data can include information concerning the television system operating characteristics or other data generated by devices used in connection with an endoscopic inspection, such as surgical or therapeutic devices. These additional inputs can be received in the same way as the keying signals 28 into the microprocessor 24 and can then be processed in the same way as the keying signals 28 by the character generator 14.

Additionally, the television system 10 can also be provided with a device, not shown, that records the signal 220 as it is supplied to the video display or monitor 13. Thus, a permanent record of the correlation between the measurements and/or operating characteristics data and endoscopic image displayed on the video display or monitor 13 can be had.

Moreover, the television system of the present invention can be provided with devices, not shown, that alert an operator whenever measurements and/or operating characteristics data exceed predetermined limits. Specifically, an acoustical or audible signal can be generated if any limit is exceeded. Furthermore, the exceeding of such limit can be indicated in the displayed image on the television monitor or video display 13 by means of flashing characters or alternating light/dark keying of the displayed characters, or any other suitable or desirable method.

Furthermore, the character generator 14 can be programmed so that the selection and geometry of the edge zones 23 can be varied as a function of inputs from the data input device 15. Accordingly, the sides, geometry, and position of the endoscopic image can be arbitrarily and freely selected also. When the entire screen of the monitor 13 is used for the endoscopic image, then the characters representing data and textual information can be faded into the image. Also, several selected endoscopic images can be faded individually or jointly into a current endoscopic image to effect representation of temporal dependant and consecutive cycles.

While a preferred embodiment has been shown, modifications and changes may become apparent to those skilled in the art which shall fall within the spirit and scope of the invention. It is intended that such modifications and changes be covered by the attached claims.

We claim:
1. An endoscopic television system, comprising:
   (a) an endoscope adapted to generate an endoscopic image video signal representative of an endoscopic image, the endoscopic image video signal having synchronization signals therein;
   (b) data input means for generating keying signals representative of characters;
   (c) character generator means coupled to the data input means for generating character signals representative of characters in response to receipt of the keying signals, and for storing the character signals in a character store;
   (d) synchronization means coupled to the endoscopic image video signal for generating a synchronization output signal representative of the synchronization pulses in the endoscopic image video signal;

(e) image control means associated with the character generator means and coupled to the synchronization output signal for reading the character signals stored in the character store as a function of the synchronization output signal, and for generating a character video signal;

(f) mixer means coupled to the endoscopic image video signal and the character video signal for mixing the signals together and to generate a composite endoscopic image/character video signal;

(g) monitor means coupled to the composite endoscopic image/character video signal for displaying on a television screen the endoscopic image and characters represented by the composite signal; the endoscopic image being displayed on a portion of the screen, the characters being displayed on at least one image-free zone of the screen.

2. An endoscopic television system as set forth in claim 1, wherein the data input means includes a keyboard.

3. An endoscopic television system as set forth in claim 1, wherein the data input means includes external apparatus associated with an endoscopic inspection.

4. An endoscopic television system as set forth in claim 1, wherein the image control means is coupled to and controlled by a microprocessor that converts the keying signals from the data input means into the character signals, the character signals being placed in the character store as a function of a program stored in a program store, the program determining specific locations in the character store at which the character signals are stored.

5. An endoscopic television system as set forth in claim 1, wherein the keying signals represent measurement data.

6. A television system according to claim 5, further comprising means for generating an audible signal whenever the measurement information exceeds a predetermined limit.

7. An endoscopic television system as set forth in claim 5, further comprising means for optically signalling the exceeding of a predetermined limit by the measurement information.

8. An endoscopic television system as set forth in claim 1, further including means for storing the composite endoscopic image/character signal.

9. A method for correlating endoscopic images with endoscopic inspection related data, comprising the steps of:

(a) generating an endoscopic image video signal representative of an endoscopic image and having video synchronization pulses incorporated therein;

(b) generating character signals representative of characters and associated with the endoscopic inspection related data;

(c) storing the character signals;

(d) extracting synchronization information from the endoscopic image video signal by detecting the synchronization pulses incorporated therein;

(e) generating a character video signal by reading out the stored character signals in synchronization with the endoscopic image video signals;

(f) mixing the endoscopic image video signal and the character video signal to generate a composite endoscopic image/character video signal; and (g) displaying the endoscopic image and characters represented by the composite signal on a television monitor.

10. A method as set forth in claim 9, further comprising a step of storing measurement data associated with endoscopic or surgical intervention devices in the character store for display on the television monitor.

11. A method as set forth in claim 10, further comprising the step of generating an audible signal whenever one of said measurement data exceeds a predetermined limit.

12. A method as set forth in claim 10, further comprising the step of optically emphasizing pertinent data on the television monitor whenever the pertinent data exceeds a predetermined limit.

13. A method as set forth in claim 9, further comprising the steps of (a) storing individual endoscopic images; (b) selecting endoscopic images for display on the television monitor; and (c) fading the selected endoscopic images onto the television monitor in accordance with a timed sequence.

14. An endoscopic television system, comprising:

(a) an endoscope adapted to generate an endoscopic image video signal representative of an endoscopic image and having synchronization pulses therein;

(b) a television or video monitor;

(c) at least one data input device adapted to generate as an output signal representative of characters;

(d) a pulse signal detection device coupled to the endoscopic image video signal and adapted to generate as an output synchronization pulse signal;

(e) a character generator coupled to the data input device output and to the pulse signal detection device output, the character generator generating character signals that are stored in a character store;

(f) an image controller, associated with the character generator and coupled to the pulse signal detection device output, that reads character signal data from the character store as prompted by the synchronization pulse signal and that generates a character video signal; and (g) a mixer coupled to the endoscopic image video signal and the character video signal that generates a composite endoscopic image/character video signal that, in turn, is transmitted to the television or video monitor so that the endoscopic image and character data are displayed simultaneously on the television or video monitor as one image.

15. An endoscopic television system as set forth in claim 14, wherein the data input device includes a keyboard and the signals generated thereby are keying signals.

16. An endoscopic television system as set forth in claim 15, wherein the data input device further includes apparatus associated with the systems.

17. An endoscopic television system as set forth in claim 14, further including a device coupled to the data input device that produces an audible signal whenever data input therethrough exceeds a limit.

18. An endoscopic television system as set forth in claim 14, wherein the character generator is controlled by a microprocessor associated therewith, the microprocessor generating and storing character signals in the character store in response to receipt of signals representative of characters from the data input device.

* * * * *